United States Patent [19]
Beschke et al.

[11] 3,960,766
[45] June 1, 1976

[54] CATALYST FOR THE PRODUCTION OF PYRIDINE AND 3-METHYLPYRIDINE

[75] Inventors: Helmut Beschke; Hans Schaefer; Gerd Schreyer, all of Grossauheim; Wilhelm Alfons Schuler, Bad Homburg; Wolfgang Weigert, Offenbach, all of Germany

[73] Assignee: Deutsche Gold- und Silber-Scheideanstalt vormals Roessler, Germany

[22] Filed: May 17, 1973

[21] Appl. No.: 361,331

[30] Foreign Application Priority Data
May 18, 1972 Germany............................ 2224160

[52] U.S. Cl.............................. 252/437; 252/439; 252/442; 252/441; 260/290 R
[51] Int. Cl.².......................................... B01J 27/06
[58] Field of Search ............ 252/439, 442, 441, 437

[56] References Cited
UNITED STATES PATENTS

| | | | |
|---|---|---|---|
| 2,289,375 | 7/1942 | Mattox............................ | 252/442 X |
| 2,364,114 | 12/1944 | Veltman ............................ | 252/442 |
| 2,400,446 | 5/1946 | Veltman .......................... | 252/442 X |
| 2,602,772 | 7/1952 | Haensel ............................ | 252/442 X |
| 3,271,300 | 9/1966 | Baker.............................. | 252/442 X |

FOREIGN PATENTS OR APPLICATIONS 1,222,971   2/1971   United Kingdom

Primary Examiner—Helen M. S. Sneed
Attorney, Agent, or Firm—Cushman, Darby & Cushman

[57] ABSTRACT

Catalysts useful in the reaction of acrolein with ammonia to form pyridine and 3-methylpyridine are prepared by heating compounds of Al, F, and O and at least two elements of the second, fourth, fifth and sixth groups of the periodic system with oxygen at 550° to 1200°C.

19 Claims, No Drawings

CATALYST FOR THE PRODUCTION OF PYRIDINE AND 3-METHYLPYRIDINE

The invention is concerned with catalysts for the reaction of acrolein with ammonia to form pyridine and 3-methylpyridine.

There are several known processes for the production of pyridine and methylpyridine from acrolein and ammonia. They differ essentially in the particular catalysts used. As such catalysts there are chiefly employed materials based on aluminium oxides and silicates. Fluorine containing aluminium oxide or aluminium silicates have been used (Moll East German Patent No. 58960) or fluosilic acid or fluoboric acid containing aluminum silicates which have been pretreated by heating to 450°C. (German published application No. 1,917,037). There has also been used zeolite containing molecular sieves containing lathanum (Parks-Smith German published application No. 2,023,158). All known processes result in small space-time-yields.

There have now been found catalysts suitable for the production of pyridine and 3-methyl pyridine by reaction of acrolein with ammonia which consists of compounds of the elements Al, F and O and at least 2 elements of the second, fourth, fifth and sixth groups of the periodic table which have been pretreated with oxygen at 550° to 1200°C. Illustrative of elements of the second, fourth, fifth and sixth groups of the periodic system which can be used include Mg, Ca, Sr, Ba, Zn, Cd, Hg, Ti, Zr, Si, Sn, Pb, V, Ge, Be, Ta, P, As, Sb, Bi, Cr, Mo, W, S, Se, Te. Surprisingly the use of these catalysts produce very high space-time-yields.

The catalysts of the invention contain besides the elements Al, F and O at least 2 of the elements of the second, fourth, fifth and sixth groups, main or side groups, of the periodic system. Especially they contain at least one element of the second group together with at least one element of the fourth, fifth or sixth group, or an element of the fourth group together with at least one additional element of the fourth group, or at least one element of the fourth group together with at least one element of the fifth or sixth group. Preferably there are used as catalysts materials which in addition to the elements Al, F and O contain one of the elements Mg, Ba, Zr or Sn together with one of the elements Ti, Zr, Sn, P, Ta, Sb or S. The elements are generally present in the catalyst in the form of oxides or as compounds with each other and oxygen.

For the production of the catalysts of the invention first there are prepared suitable mixtures of starting materials containing the corresponding elements and then these are treated with oxygen at temperatures between 550° and 1200°C.

The aluminum is generally added as the oxide. However, it can also be employed as the metal or any compound of aluminum which can be converted into aluminum oxide, as, for example, aluminum nitrate or aluminum acetate. Also the elements of the second, fourth, fifth and sixth group of the periodic system provided as the further catalyst constituents can generally be used as the oxides. Also there can be used the elements themselves or any compounds of the elements which can be converted by reacting with oxygen. These especially include salts which are decomposed upon heating, as, for example, the nitrate, acetate, propionate, oxalate, malonate, succinate, etc.

The fluorine is added as a solid, liquid or gaseous compound, especially as a compound which is soluble or hydrolyzable in water. For example, there can be used ammonium fluoride, ammonium hydrogen fluoride and hydrofluoric acid. It is advantageous to add at least one of the elements of the second, fourth, fifth and sixth groups employed as an additional catalyst constituent as a fluorine containing compound. Such compounds include, for example, magnesium fluoride, titanium (IV) fluoride, ammonium hexafluorozirconate, ammonium trifluorostannate, ammonium hexafluorophosphate, ammonium tetrafluoroantimonate, ammonium fluorosulfonate, ammonium fluogermanate, ammonium fluosilicate, ammonium fluotitanate, antimony trifluoride, antimony pentafluoride, arsenic trifluoride, arsenic pentafluoride, barium fluoride, barium fluosilicate, beryllium fluoride, bismuth trifluoride, cadmium fluoride, cadmium fluosilicate, calcium fluoride, calcium fluosilicate, chromium (II) fluoride, chromium (III) fluoride, fluosulfonic acid, germanium difluoride, germanium tetrafluoride, lead (II) fluoride, lead fluosilicate, magnesium fluosilicate, mercury fluoride, molybdenum hexafluoride, selenium hexafluoride, selenium tetrafluoride, strontium fluoride, sulfuryl fluoride, tantalum hexafluoride, tellurium hexafluoride, tellurium tetrafluoride, tin (II) fluoride, tin (IV) fluoride, titanium (III) fluoride, tungsten hexafluoride, zinc fluoride, zirconium (IV) fluoride.

The mixture of starting materials is generally chosen so that the atomic ratio of Al to F is between 1,000 to 10 and 1,000 to 800, especially between 1,000 to 20 and 1,000 to 400, the atomic ratio of Al to the elements of the second, fourth, fifth and sixth groups, calculated in total, however without considering the oxygen is suitably between 1,000 to 5 and 1,000 to 200, especially between 1,000 to 10 and 1,000 to 100. The two elements of groups two, four, five and six of the periodic system should be used in an atomic ratio that each of them is present in an amount of at least 5 % of the total atoms of the second, fourth, fifth and sixth group (not counting the oxygen).

There are many possibilities for the preparation of mixtures of the starting materials. Which method is used generally depends on the type of material. Although the various compounds can be brought together in any order, it has been found advantageous to always add the fluorine containing compound last. It is suitable to add one or more of the materials as aqueous solutions or suspensions in water and in order to recover the catalyst material to evaporate these aqueous mixtures or to dry at temperatures between 100° and 200°C.

For example, the aluminum oxide in the form of powder, granular or extruded to shaped materials, such as tablets or balls can be mixed with aqueous solutions of the remaining substances. There can also be added an aqueous solution of aluminum compounds and the aluminum precipitated from this as the hydroxide, before, during or after the precipitation the remaining materials can be added, in a given case in portions. In the case that gaseous fluorine compounds are used, the aluminum oxide or its mixture with the other materials, suitably in the presence of moisture is gassed with the fluoride compound. It can furthermore be advantageous to first mix two of the materials together using water and to dry this mixture before adding an additional material.

The mixtures thus prepared are heated to temperatures between 500° and 1200°C. and treated at these temperatures for some time in the presence of oxygen. The procedure employed for the process as well as the temperature and duration of the treatment depend on the type of starting material and the procedure employed for preparation of the mixtures.

The mixtures can be heated directly to the temperature of treatment. However, it can be advantageous to first only heat the mixtures moderately and to increase the temperatures slowly, in a given case in the course of several hours, uniformly or preferably stepwise, to the treatment temperature between 550° and 1200°C.

For the actual treatment with oxygen the mixtures are heated to temperatures between 550° and 1200°C., preferably between 600° and 800°C. It can be advantageous to treat the mixtures in succession at different temperatures within this range. In this connection there can be used either temperature increases or temperature decreases. The treatment generally lasts for about 2 to 20 hours, in most cases about 3 to 10 hours. Air is generally used as the source of oxygen. There can be used, however, pure oxygen or oxygen mixed with other inert gases.

The corresponding compounds are formed in the mixtures in the treatment with oxygen, in case the starting materials are not oxides or other compounds with oxygen. The conversion into these oxygen containing compounds, however, can take place entirely or partially before or during the preparation of the mixtures.

A preferred method of operation is to treat aluminum oxide which has a surface area (BET) between 80 and 400 m$^2$/g, especially a surface area (BET) between 200 and 350 m$^2$/g, and in a given case is present in the form of extrusions, with an aqueous solution of the nitrate or oxalate of the other elements concerned, drying this mixture by heating to about 100°C., treating the dry material with an aqueous solution of a fluorine compound, drying this mixture by heating to about 100°C. and finally treating this dry material for 3 to 10 hours at 600° to 800°C. with oxygen. It is especially advantageous to add at least one of the elements of the second, fourth, fifth or sixth group as a fluorine compound, the remaining element or elements as nitrate or oxalate.

The catalysts are suited for use in fixed bed or fluidized bed and correspondingly are used, for example, in the form of extrusions or in granular form.

The reaction of acrolein with ammonia to form pyridine and 3-methyl pyridine using the catalysts of the invention, takes place in customary manner in the gas phase. It is chiefly carried out at normal pressure or under slight super atmospheric pressure up to about 3 atmospheres at temperatures between 300° and 500°C., especially between 350° and 450°C. The proportions of ammonia to acrolein are generally so chosen that there is present more ammonia than that required stochiometrically for 0.5 mole for each mole of acrolein. There is used especially between 1 and 10 moles of ammonia, preferably between 1 and 3 moles of ammonia, for each mole of acrolein. Ammonia and acrolein are advantageously added with diluents. As suitable gases for admixture there can be added, for example, nitrogen, air, oxygen, steam or organic carrier gases, such as benzene. In a given case there can be controlled by the oxygen content of the gas mixture whether the formation of pyridine or 3-methyl pyridine will be favored. With a content of 1 to 4 moles of oxygen per mole acrolein the formation of pyridine is preferred, at a lesser oxygen content formation of 3-methyl pyridine is favored. It is advantageous to first dilute the acrolein with the alien gas and to mix in the ammonia directly before the reaction zone at temperatures of 200° to 400°C. The reaction conditions such as temperature, dilution of the gas and speed of flow are suitably so tuned to each other that the residence time in the reaction zone is 0.5 to 5.0 seconds, especially 0.8 to 2.5 seconds. The recovery of the pyridine and 3-methyl pyridine takes place in the customary manner. In the following examples there are used the concepts:

$$\text{Yield} = \frac{\text{Moles of Product Formed}}{\text{Moles of Acrolein Added}} \times 2 \times 100 \, (\%)$$

$$\text{Space-Time-Yield} = \frac{\text{Amount of Product Formed/Time}}{\text{Bulk Volume of Catalyst}} \left(\frac{g}{l \times h}\right)$$

As product is meant the sum of pyridine and 3-methyl pyridine. The gas volumes recited are based on room temperature.

EXAMPLES

EXAMPLE 1a 1.300.grams of aluminum oxide in the form of extrusions 2 mm in diameter and 4 to 6 mm long with a surface area (BET) of 300 m$^2$/g were treated with a solution of 160 grams (0.62 mole) of analytically pure magnesium nitrate hexahydrate (Mg (NO$_3$)$_2$.6H$_2$O) in 1000 ml of water and 30 ml of concentrated nitric acid. The mixture was subsequently dried while it was held for 8 hours at 100°C. The dry material was stirred with a solution of 77.5 grams (0.62 mole) of titanium (IV) fluoride (Ti F$_4$) in 900 ml of water. This mixture was dried while it was held at 100°C. for 12 hours. The dry material was subsequently heated in an airstream for 4 hours to 700°C. The atomic proportions Al to Mg to Ti to F were 1,000 to 25 to 25 to 100.

A gaseous mixture of 840 grams (15.0 moles) of acrolein, 735 liters (30.6 moles) of nitrogen and 700 liters (29.2 moles) of ammonia were led hourly in homogeneous flow over 1 liter (bulk volume) of the catalyst thus prepared. The ammonia gas was mixed with the acrolein-nitrogen mixture directly at the entrance to the reactor through a binary nozzle. The gases had an entrance temperature of 220°C. The catalyst was preheated to 380°C.; in the course of the reaction the temperature was 400° to 440°C. The reaction gases were washed with water. The product continuously extracted from the aqueous washing liquid with benzene. The fractional distillation of this extract hourly resulted in 136.0 grams (1.72 mole) of pyridine and 290 grams (3.12 moles) 3-methyl pyridine. The yield was 65%, the space-time-yield 426 g/l × h.

EXAMPLE 1b

The procedure of example 1a was carried out except that there was fed in hourly a gaseous mixture of 560 grams (10.0 moles) of acrolein, 490 liters (20.4 moles) of nitrogen and 467 liters (19.5 moles) of ammonia.

There resulted hourly 97 grams (1.23 moles) of pyridine and 216 grams (2.32 moles) of 3-methyl pyridine. The yield amounted to 71%, the space-time-yield 313 g/l × h.

EXAMPLES 2 to 11

The procedure was the same as example 1a, however, deviating in the constituents of the catalyst. For the production there was first added to the aluminum oxide an aqueous, nitric acid solution of the nitrate or oxalate of one of the elements concerned and after drying this mixture treated with an aqueous solution of a fluorine compound of the other element of the second, fourth, fifth or sixth group which was employed. After drying this mixture the material was heated for 4 hours in the stream of air. The individual data are as follows:

EXAMPLE 2

| | |
|---|---|
| Catalyst produced from | 1300 grams $Al_2O_3$ |
| | 145 grams $ZrO(NO_3)_2$ |
| | 78 grams $TiF_4$ |
| Atomic Ratio Al to Zr to Ti to F | = 1000 to 25 to 25 to 100 |
| Substance heated to | 670°C. |
| Hourly produced pyridine | 137 grams (1.73 moles) |
| 3-methyl pyridine | 300 grams (3.22 moles) |
| Yield | 66% |
| Space-Time-Yield | 437 grams/l × h |

EXAMPLE 3

| | |
|---|---|
| Catalyst produced from | 1300 grams $Al_2O_3$ |
| | 130 grams $Sn(COO)_2$ |
| | 151 grams $(NH_4)_2ZrF_6$ |
| Atomic Ratio Al to Sn to Zr to F | = 1000 to 25 to 25 to 150 |
| Substance heated to | 700°C. |
| Hourly produced pyridine | 139 grams (1.76 moles) |
| 3-methyl pyridine | 297 grams (3.19 moles) |
| Yield | 66% |
| Space-Time-Yield | 436 g/l × h |

EXAMPLE 4

| | |
|---|---|
| Catalyst produced from | 1300 grams $Al_2O_3$ |
| | 127 grams $ZrO(NO_3)_2$ |
| | 107 grams $NH_4SnF_3$ |
| Atomic Ratio Al to Zr to Sn to F | = 1000 to 23 to 23 to 69 |
| Substance heated to | 720°C. |
| Hourly produced pyridine | 134 grams (1.70 moles) |
| 3-methyl pyridine | 289 grams (3.10 moles) |
| Yield | 64 % |
| Space-Time-Yield | 423 g/l × h |

EXAMPLE 5

| | |
|---|---|
| Catalyst produced from | 1300 grams $Al_2O_3$ |
| | 180 grams $Mg(NO_3)_2 \cdot 6H_2O$ |
| | 115 grams $NH_4PF_6$ |
| Atomic Ratio Al to Mg to P to F | = 1000 to 28 to 28 to 168 |
| Substance heated to | 700°C. |
| Hourly produced pyridine | 137 grams (1.73 moles) |
| 3-methyl pyridine | 258 grams (2.77 moles) |
| Yield | 60 % |
| Space-Time-Yield | 395 g/l × h |

EXAMPLE 6

| | |
|---|---|
| Catalyst produced from | 1300 grams $Al_2O_3$ |
| | 145 grams $ZrO(NO_3)_2$ |
| | 102 grams $NH_4PF_6$ |
| Atomic Ratio Al to Zr to P to F | = 1000 to 25 to 25 to 150 |
| Substance heated to | 700°C. |
| Hourly produced pyridine | 150 grams (1.90 moles) |
| 3-methyl pyridine | 258 grams (2.77 moles) |
| Yield | 62 % |
| Space-Time-Yield | 408 g/l × h |

EXAMPLE 7

| | |
|---|---|
| Catalyst produced from | 1300 grams $Al_2O_3$ |
| | 160 grams $Mg(NO_3)_2 \cdot 6H_2O$ |
| | 135 grams $NH_4SbF_6$ |
| Atomic Ratio Al to Mg to Sb to F | = 1000 to 25 to 25 to 100 |
| Substance heated to | 700°C. |
| Hourly produced pyridine | 135 grams (1.70 moles) |
| 3-methyl pyridine | 261 grams (2.80 moles) |
| Yield | 60 % |
| Space-Time-Yield | 396 grams/l × h |

EXAMPLE 8

| | |
|---|---|
| Catalyst produced from | 1300 grams $Al_2O_3$ |
| | 160 grams $Mg(NO_3)_2 \cdot 6H_2O$ |
| | 73 grams $NH_4FSO_3$ |
| Atomic Ratio Al to Mg to S to F | = 1000 to 25 to 25 to 25 |
| Substance heated to | 700°C. |
| Hourly produced pyridine | 141 grams (1.78 moles) |
| 3-methyl pyridine | 275 grams (2.95 moles) |
| Yield | 63 % |
| Space-Time-Yield | 416 g/l × h |

EXAMPLE 9

| | |
|---|---|
| Catalyst produced from | 1300 grams $Al_2O_3$ |
| | 130 grams $Sn(COO)_2$ |
| | 73 grams $NH_4FSO_3$ |
| Atomic Ratio Al to Sn to S to F | = 1000 to 25 to 25 to 25 |
| Substance heated to | 700°C. |
| Hourly produced pyridine | 139 grams (1.76 moles) |
| 3-methyl pyridine | 268 grams (2.88 moles) |
| Yield | 62 % |
| Space-Time-Yield | 407 g/l × h |

EXAMPLE 10

| | |
|---|---|
| Catalyst produced from | 1300 grams $Al_2O_3$ |
| | 180 grams $Mg(NO_3)_2 \cdot 6H_2O$ |
| | 195 grams $TaF_5$ |
| Atomic Ratio Al to Mg to Ta to F | = 1000 to 28 to 28 to 140 |
| Substance heated to | 690°C. |
| Hourly produced pyridine | 146 grams (1.85 moles) |
| 3-methyl pyridine | 302 grams (3.25 moles) |
| Yield | 68 % |
| Space-Time-Yield | 448 g/l × h |

EXAMPLE 11

| | |
|---|---|
| Catalyst produced from | 1300 grams $Al_2O_3$ |
| | 184 grams $Ba(NO_3)_2$ |
| | 195 grams $TaF_5$ |
| Atomic Ratio to Al to Ba to Ta to F | = 1000 to 28 to 28 to 90 |
| Substance heated to | 710°C. |
| Hourly produced pyridine | 133 grams (1.68 moles) |
| 3-methyl pyridine | 283 grams (3.04 moles) |
| Yield | 63 % |
| Space-Time-Yield | 416 g/l × h |

EXAMPLE 12

1,360 grams of aluminum hydroxide with an $Al_2O_3$ content of 75% and a bulk volume of 690 g/l whose particle size was 70% below 0.045 mm. and 99% below 0.100 mm., was suspended in 1.500 ml of water. This suspension was treated successively with stirring with 80 grams of finely divided titanium dioxide, a solution of 130 grams of magnesium nitrate ($Mg(NO_3)_2 \cdot 6H_2O$) in 300 ml of water and a solution of 57 grams of ammonium hydrogen fluoride ($NH_4HF_2$) in 100 ml of water. The mixture was held at 90°C. 1 hour with stirring and then dried in a roll dryer. After adding 3% of graphite the material was tableted and after that heated in an airstream for 2 hours at 500°C. and then 4 hours at 700°C. The atomic ratio Al to Mg to Ti to F was 1,000 to 25 to 50 to 100. The catalyst thus prepared was used as in example 1a. There were recovered hourly 142 grams (1.80 moles) of pyridine and 300 grams (3.22 moles) of 3-methyl pyridine. The yield was 67%, the space-time-yield 442 g/l × h.

What is claimed is:

1. A catalyst suitable for the reaction of acrolein with ammonia to form pyridine and 3-methylpyridine consisting essentially of the product obtained by treating with oxygen at a temperature of 550° to 1200°C. compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb and S, the ratios of the elements being Al to F of between 1,000 to 10 and 1,000 to 800 and of Al to the elements of the second, fourth, fifth and sixth groups being between 1,000 to 5 and 1,000 to 200.

2. A catalyst according to claim 1 wherein the catalyst is formed by treating with oxygen at 550° to 1200°C. (1) aluminum, aluminum oxide or an aluminum compound which can be converted to the oxide by treatment with oxygen (2) at least two other elements of the second, fourth, fifth or sixth group of the periodic system, said two other elements being selected from the group consisting of Mg, Ba, Zr, Sn, Ti, P, Ta, Sb and S or oxides thereof or compounds thereof which can be converted to the oxide with oxygen and (3) ammonium fluoride, ammonium hydrogen fluoride, hydrogen fluoride or a fluoride of Mg, Ba, Zr, Sn, Ti, P, Ta, Sb or S.

3. A process according to claim 2 comprising treating with oxygen at a temperature of 550° to 1200°C. a mixture of the elements (1) Al, (2) F and (3) at least two other elements selected from the second, fourth, fifth and sixth groups of the periodic system, said two other elements being selected from the group consisting of Mg, Ba, Zr, Sn, Ti, P, Ta, Sb and S, oxides of such elements or compounds of such elements which are convertible to the oxides.

4. A catalyst according to claim 2 consisting of Al, F, O, Mg and Ti.

5. A catalyst according to claim 2 wherein the ratios of the elements are Al to F of between 1,000 to 20 and 1,000 to 400 and of Al to the elements of the second, fourth, fifth and sixth groups of between 1,000 to 10 and 1,000 to 100.

6. A catalyst according to claim 5 wherein the catalyst consists of the elements Al, F and O together with one of the elements Mg, Ba, Zr or Sn together with a different element Ti, Zr, P, Ta, Sb or S.

7. A catalyst according to claim 2 wherein the catalyst consists of the elements Al, F and O together with one of the elements Mg, Ba, Zr or Sn together with a different element Ti, Zr, P, Ta, Sb or S.

8. A process according to claim 3 wherein the atomic ratios are Al to F of from 1,000 to 10 to 1,000 to 800 and of Al to the additional elements of the second, fourth, fifth and sixth groups of from 1,000 to 5 to 1,000 to 200.

9. A process according to claim 8 wherein the mixing of elements, oxides of elements or compounds of the elements which are convertible to oxides is carried out in the presence of water.

10. A process according to claim 9 wherein the aluminum is added as aluminum oxide or aluminum hydroxide, the fluorine is added as ammonium fluoride, ammonium hydrogen fluoride, hydrogen fluoride or as a fluoride of at least one of said elements of the second, fourth, fifth and sixth groups and the elements of said second, fourth, fifth and sixth groups are employed as said fluoride or as the nitrate, acetate or oxalate.

11. A catalyst according to claim 2 consisting of Al, F, O, Zr and Ti.

12. A catalyst according to claim 2 consisting of Al, F, O, Zr and Sn.

13. A catalyst according to claim 2 consisting of Al, F, O, Mg and P.

14. A catalyst according to claim 2 consisting of Al, F, O, Zr and P.

15. A catalyst according to claim 2 consisting of Al, F, O, Mg and Sb.

16. A catalyst according to claim 2 consisting of Al, F, O, Mg and S.

17. A catalyst according to claim 2 consisting of Al, F, O, Sn and S.

18. A catalyst according to claim 2 consisting of Al, F, O, Mg and Ta.

19. A catalyst according to claim 2 consisting of Al, F, O, Ba and Ta.

* * * * *